(12) United States Patent
Markowitz et al.

(10) Patent No.: US 12,376,837 B2
(45) Date of Patent: *Aug. 5, 2025

(54) DEVICE FOR COLLECTING A BIOLOGICAL SAMPLE

(71) Applicant: Case Western Reserve University, Cleveland, OH (US)

(72) Inventors: Sanford Markowitz, Cleveland, OH (US); Amitabh Chak, Cleveland, OH (US); Joseph Willis, Cleveland, OH (US); Jeffrey Silver Taggart, Cleveland, OH (US); Rebecca Blice, Cleveland, OH (US); Dean Secrest, Cleveland, OH (US); Dennis Siedlak, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/643,335

(22) Filed: Dec. 8, 2021

(65) Prior Publication Data

US 2022/0096063 A1    Mar. 31, 2022

Related U.S. Application Data

(60) Continuation of application No. 16/405,634, filed on May 7, 2019, which is a division of application No.
(Continued)

(51) Int. Cl.
    *A61B 10/02* (2006.01)
(52) U.S. Cl.
    CPC ...... *A61B 10/02* (2013.01); *A61B 2010/0216* (2013.01); *A61B 2010/0225* (2013.01)

(58) Field of Classification Search
    None
    See application file for complete search history.

(56) References Cited

U.S. PATENT DOCUMENTS

| 1,098,222 A | * | 5/1914 | Brasefield | ........... A61M 5/2425 |
| | | | | 604/275 |
| 2,701,559 A | * | 2/1955 | Cooper | ................. A61B 10/02 |
| | | | | 73/864.33 |

(Continued)

FOREIGN PATENT DOCUMENTS

| CN | 202104944 U | 1/2012 |
| CN | 105193459 A | 12/2015 |

(Continued)

OTHER PUBLICATIONS

"Motility Diagnostic Services | UC Davis Health", health.ucdavis.edu/internalmedicine/gastro/esophmanometry.html, 2 pages, printed on Apr. 25, 2023. (Year: 2023).*

(Continued)

*Primary Examiner* — Matthew Kremer
(74) *Attorney, Agent, or Firm* — Greenberg Traurig, LLP; Chinh H. Pham; Joshua I. Rudawitz

(57) ABSTRACT

A device for collecting a biological sample in a patient includes a collection portion having a first axial end portion and a second axial end portion. The second axial end portion has a collapsed position and an expanded position. The second axial end portion moves in an axial direction relative to the first axial end portion when the second axial end portion moves between the collapsed position and the expanded position. The second axial end portion extends axially into the first axial end portion and has a concave shape when in the collapsed position. The second axial end portion is convex when in the expanded position.

22 Claims, 6 Drawing Sheets

Related U.S. Application Data

15/103,638, filed as application No. PCT/US2014/070060 on Dec. 12, 2014, now Pat. No. 10,660,621.

(60) Provisional application No. 61/915,029, filed on Dec. 12, 2013.

(56) References Cited

U.S. PATENT DOCUMENTS

| | | | |
|---|---|---|---|
| 3,400,708 A | 9/1968 | Scheidt | |
| 3,664,328 A * | 5/1972 | Moyle, Jr. | A61B 10/0291 600/569 |
| 4,467,816 A * | 8/1984 | Schluter | A61B 10/04 600/569 |
| 4,481,952 A | 11/1984 | Pawelec | |
| 4,627,444 A | 12/1986 | Brooker | |
| 4,735,214 A | 4/1988 | Berman | |
| 4,979,951 A | 12/1990 | Simpson | |
| 5,318,587 A | 6/1994 | Davey | |
| 5,445,164 A | 8/1995 | Worthen et al. | |
| 5,879,499 A | 3/1999 | Corvi | |
| 7,004,913 B1 | 2/2006 | Rutenberg et al. | |
| 7,108,661 B2 | 9/2006 | Secrest et al. | |
| 7,485,420 B2 | 2/2009 | Markowitz | |
| 7,964,353 B2 | 6/2011 | Markowitz | |
| 8,068,897 B1 | 11/2011 | Gazdzinski | |
| 8,221,977 B2 | 7/2012 | Markowitz | |
| 8,415,100 B2 | 4/2013 | Markowitz et al. | |
| 8,481,707 B2 | 7/2013 | Markowitz et al. | |
| 8,642,271 B2 | 2/2014 | Markowitz et al. | |
| 8,668,654 B1 | 3/2014 | Gerrans et al. | |
| 9,339,259 B2 | 5/2016 | Loktionov et al. | |
| 9,580,754 B2 | 2/2017 | Markowitz et al. | |
| 10,660,621 B2 * | 5/2020 | Markowitz | A61B 10/02 |
| 2002/0173816 A1 | 11/2002 | Hung | |
| 2003/0004535 A1 | 1/2003 | Musbach et al. | |
| 2003/0040681 A1 | 2/2003 | Ng et al. | |
| 2003/0208134 A1 | 11/2003 | Secrest et al. | |
| 2004/0127932 A1 * | 7/2004 | Shah | A61M 25/1029 606/193 |
| 2005/0043649 A1 | 2/2005 | Urie | |
| 2005/0215959 A1 | 9/2005 | Whitington | |
| 2006/0184191 A1 | 8/2006 | O'Brien | |
| 2006/0189891 A1 | 8/2006 | Waxman et al. | |
| 2006/0271061 A1 | 11/2006 | Beyar et al. | |
| 2007/0239066 A1 | 10/2007 | Laham et al. | |
| 2008/0097238 A1 | 4/2008 | Loktionov et al. | |
| 2008/0188769 A1 | 8/2008 | Lu | |
| 2008/0243031 A1 * | 10/2008 | Seibel | A61B 1/0008 600/566 |
| 2009/0024060 A1 | 1/2009 | Darrigrand et al. | |
| 2009/0118641 A1 | 5/2009 | Van Dam et al. | |
| 2009/0299401 A1 | 12/2009 | Tilson | |
| 2010/0280490 A1 | 11/2010 | Schertiger | |
| 2010/0286593 A1 | 11/2010 | Krolik et al. | |
| 2011/0071428 A1 * | 3/2011 | Frecker | A61B 17/30 600/566 |
| 2012/0164638 A1 | 6/2012 | Vogelstein et al. | |
| 2013/0066346 A1 | 3/2013 | Piggot | |
| 2013/0116596 A1 | 5/2013 | Birnboim et al. | |
| 2013/0131329 A1 | 5/2013 | Markowitz et al. | |
| 2013/0267870 A1 * | 10/2013 | Lonky | A61B 10/02 600/569 |
| 2014/0113290 A1 | 4/2014 | Markowitz et al. | |
| 2014/0171828 A1 | 6/2014 | Blitzer et al. | |
| 2014/0214085 A1 * | 7/2014 | Druma | A61B 17/8855 606/279 |
| 2014/0296742 A1 | 10/2014 | Kalloo et al. | |
| 2014/0323908 A1 | 10/2014 | Fitzgerald et al. | |
| 2015/0057517 A1 | 2/2015 | Pease et al. | |
| 2015/0289752 A1 | 10/2015 | Rachlin et al. | |
| 2015/0351729 A1 | 12/2015 | Chin et al. | |
| 2015/0374436 A1 | 12/2015 | Subramaniam et al. | |
| 2016/0081671 A1 | 3/2016 | Lubinski et al. | |
| 2016/0317132 A1 | 11/2016 | Markowitz et al. | |
| 2017/0112477 A1 | 4/2017 | Benning et al. | |
| 2018/0116645 A1 | 5/2018 | Nosler et al. | |
| 2018/0146839 A1 | 5/2018 | Friedlander et al. | |
| 2018/0161020 A1 | 6/2018 | Friedlander | |
| 2019/0081671 A1 | 1/2019 | Peris | |
| 2019/0261962 A1 | 8/2019 | Markowitz et al. | |
| 2019/0365276 A1 | 12/2019 | Vaezi et al. | |
| 2020/0022685 A1 | 1/2020 | Brodbeck et al. | |
| 2020/0077992 A1 | 3/2020 | Markowitz et al. | |
| 2021/0315551 A1 | 10/2021 | Smadi et al. | |
| 2021/0369256 A1 | 12/2021 | Markowitz et al. | |
| 2021/0386410 A1 | 12/2021 | Chak et al. | |
| 2022/0096060 A1 | 3/2022 | Markowitz et al. | |
| 2022/0096061 A1 | 3/2022 | Markowitz et al. | |
| 2022/0096062 A1 | 3/2022 | Markowitz et al. | |
| 2022/0096063 A1 | 3/2022 | Markowitz et al. | |
| 2022/0096064 A1 | 3/2022 | Markowitz et al. | |
| 2023/0000474 A1 | 1/2023 | Markowitz et al. | |
| 2023/0000475 A1 | 1/2023 | Markowitz et al. | |

FOREIGN PATENT DOCUMENTS

| | | | |
|---|---|---|---|
| GB | 1573819 A | 8/1980 | |
| JP | 59064065 A | 4/1984 | |
| JP | 60052817 A | 3/1985 | |
| JP | 2005168910 A | 6/2005 | |
| JP | 2007222387 A | 9/2007 | |
| JP | 2008541851 A | 11/2008 | |
| JP | 2010505592 A | 2/2010 | |
| JP | 2015196040 A | 11/2015 | |
| JP | 2016516491 A | 6/2016 | |
| JP | 2017038884 A | 2/2017 | |
| JP | 2017064067 A | 4/2017 | |
| WO | 198705523 A1 | 9/1987 | |
| WO | 1989006360 A1 | 7/1989 | |
| WO | 199423787 A1 | 10/1994 | |
| WO | 2000054829 A2 | 9/2000 | |
| WO | 2004110300 A3 | 12/2004 | |
| WO | 2006003447 A1 | 1/2006 | |
| WO | 2012162610 A1 | 11/2012 | |
| WO | 2013040160 A1 | 3/2013 | |
| WO | 2013116560 A1 | 8/2013 | |
| WO | 2014121207 A1 | 8/2014 | |
| WO | 2014143459 A1 | 9/2014 | |
| WO | 2014170393 A1 | 10/2014 | |
| WO | 2015089422 A1 | 6/2015 | |
| WO | WO-2016034888 A1 * | 3/2016 | A61B 10/02 |
| WO | 2016178189 A1 | 11/2016 | |
| WO | 2017147586 A1 | 8/2017 | |
| WO | 2018204659 A1 | 11/2018 | |

OTHER PUBLICATIONS

Capsule Size Guide, LFA Machines Oxford Ltd., https://www.lfacapsulefillers.com/capsule-size-chart.

Esophagus, Britannica's public website, www.britannica.com/science/human-digestive-system/Esophagus, 16 pages, printed on Jun. 27, 2022 (Year: 2022).

Businello et al., "The Pathologic and Molecular Landscape of Esophageal Squamous Cell Carcinogenesis," Cancers, Aug. 4, 2020, vol. 12, No. 2160, pp. 1-20.

Clancy et al., "Diagnosing Invasive Candidiasis," Journal of Clinical Microbiology, May 2018, vol. 56, No. 5, pp. e01909-17.

Dioverti et al., "Cytomegalovirus," Microbiology Spectrum, Jul. 15, 2016, vol. 4, No. 4.

Srinagesh et al., "Biomarkers in Acute Graft-versus-Host Disease: New Insights," Therapeutic Advances in Hematology, 2019, vol. 10, pp. 1-8.

Intubation, www.merriam-webster.com/dictionary/intubation, 11 pages, printed on Mar. 17, 2022.

* cited by examiner

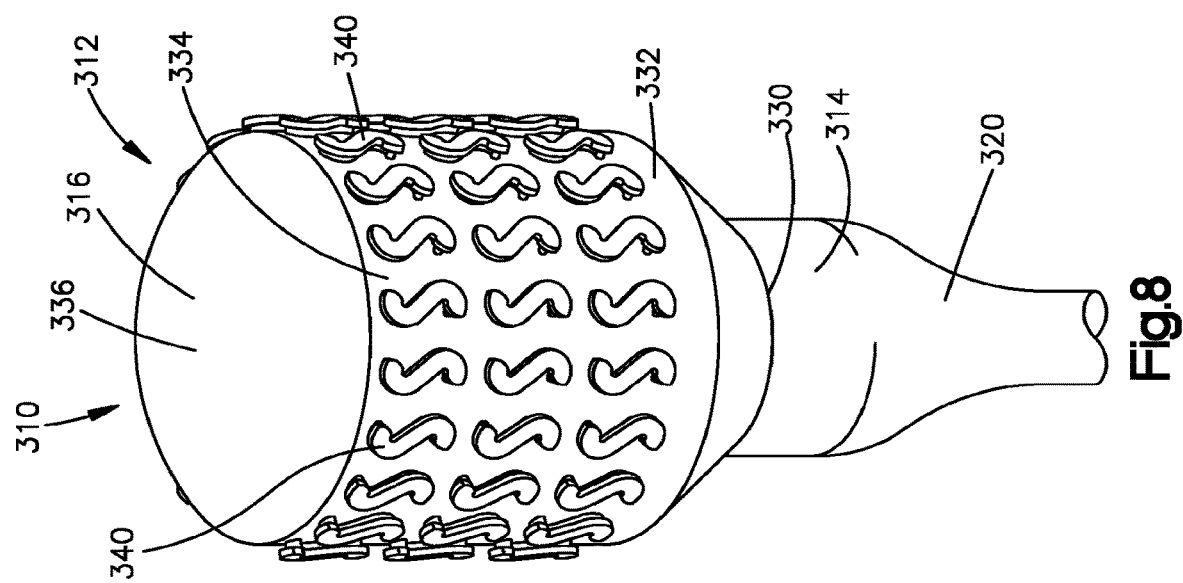
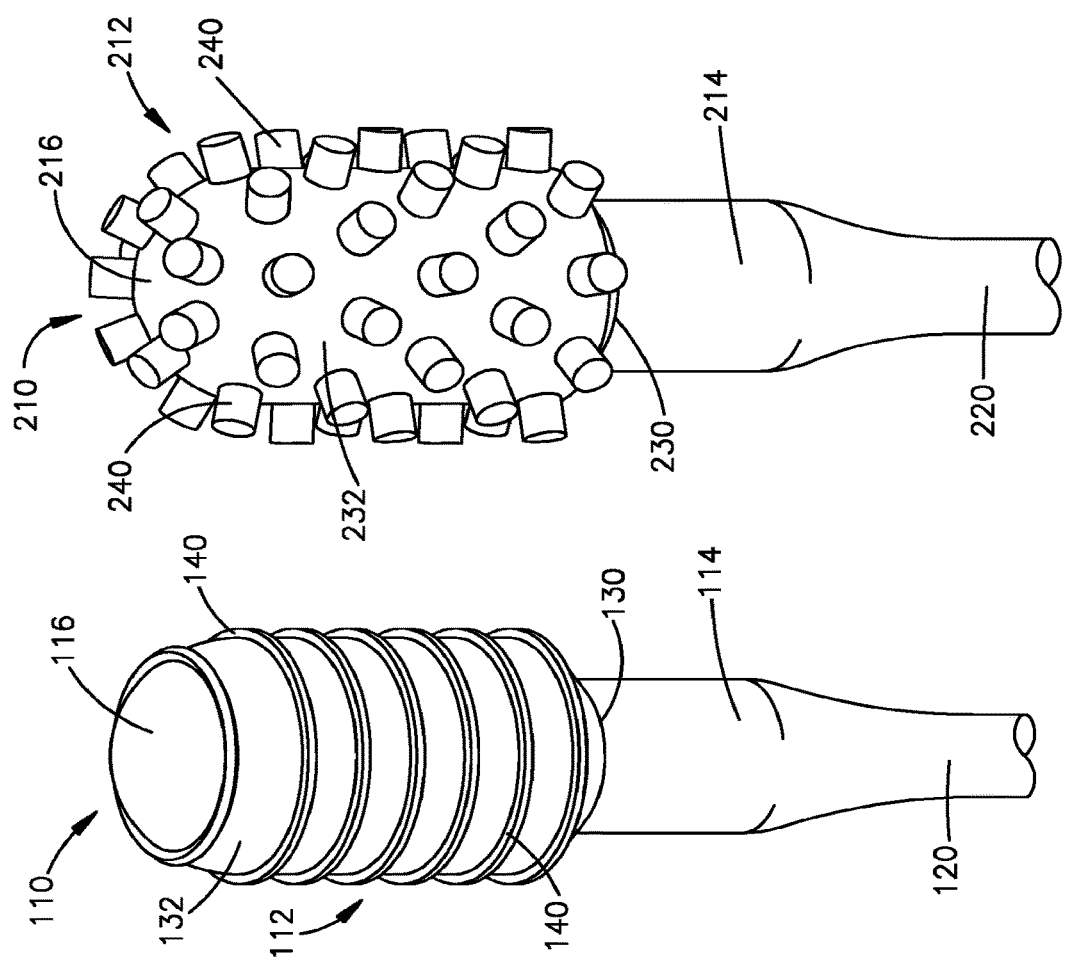
Fig.8
Fig.7
Fig.6

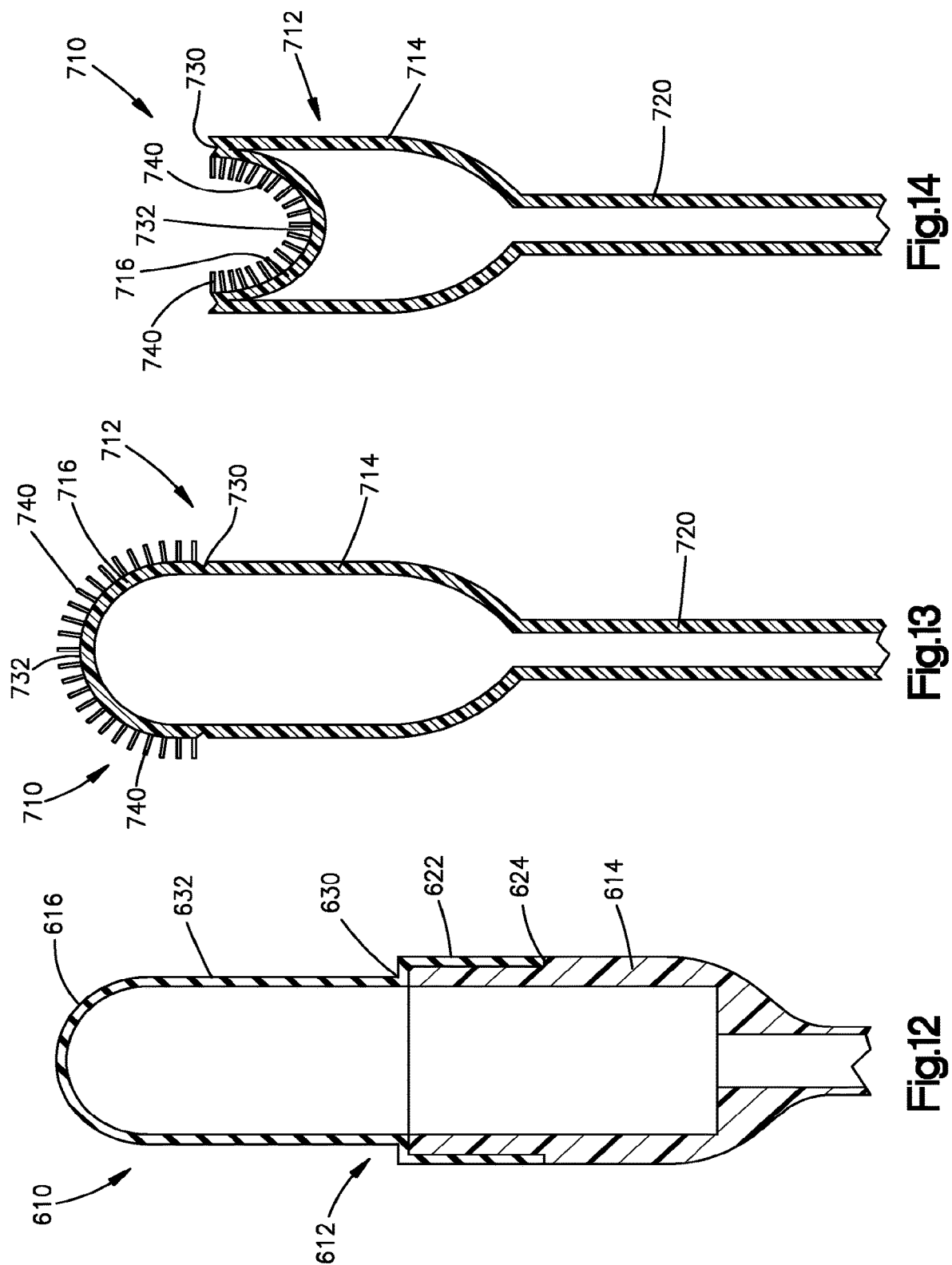

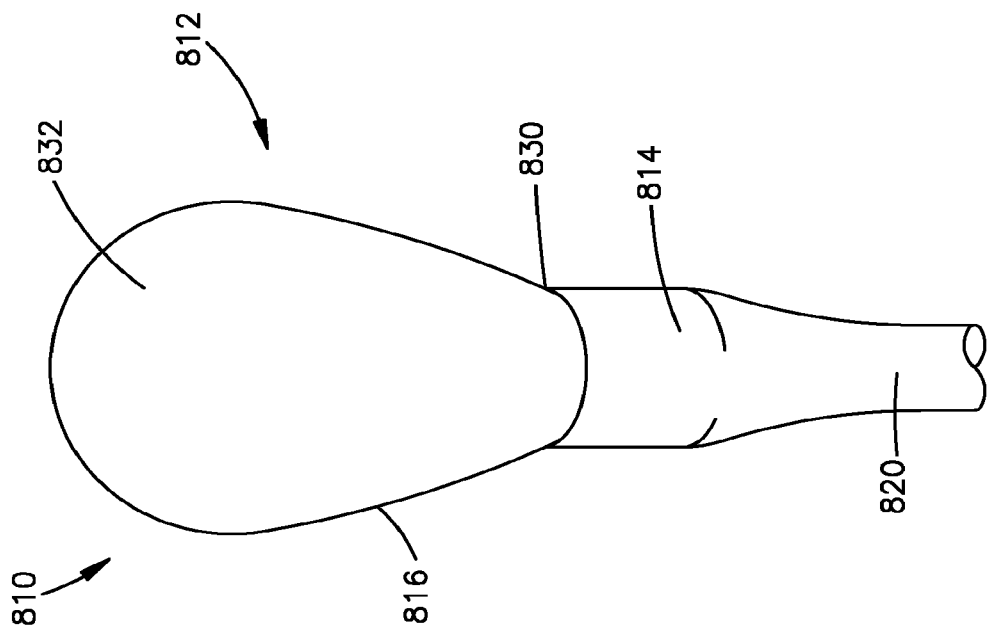

DEVICE FOR COLLECTING A BIOLOGICAL SAMPLE

RELATED APPLICATIONS

This application is a continuation application of U.S. application Ser. No. 16/405,634, filed May 7, 2019, which is a divisional of U.S. application Ser. No. 15/103,638, filed Jun. 10, 2016, now U.S. Pat. No. 10,660,621, which is a U.S. 371 National Stage of PCT/US2014/070060, filed Dec. 12, 2014, which claims priority to and the benefit of Provisional Application No. 61/915,029, filed Dec. 12, 2013, the subject matter of each of which are incorporated herein by reference in their entireties.

GOVERNMENT SUPPORT

This invention was made with government support under Grant Nos. P50CA150964, UO1CA152756, U54CA163060 awarded by The National Institutes of Health. The United States government has certain rights to the invention.

BACKGROUND OF THE INVENTION

The present invention is directed to a device for collecting a biological sample, and more specifically, to a device for collecting a biological sample, such as tissue, cells, protein, RNA and/or DNA from an esophagus of a patient.

A known issue collection device includes an expandable device with longitudinally extending folds. The expandable device expands radially at a collection site within a body lumen, such as an esophagus. After the device is expanded, tissue is collected from the collection site. The expandable device is deflated after tissue is collected. The folds trap collected tissue when the device is deflated after collection of tissue. The known tissue collection device may be inserted through an endoscope to the collection site or via standard catheter intubation techniques.

SUMMARY OF THE INVENTION

The present invention relates to a device for collection a biological a sample in a patient. The device includes a collection portion having a first axial end portion and a second axial end portion. The second axial end portion has a collapsed position and an expanded position. The second axial end portion moves in an axial direction relative to the first axial end portion when the second axial end portion moves between the collapsed position and the expanded position.

In another aspect of the present invention, a device for collecting a biological sample in a patient includes a collection portion having a first axial end portion and a second axial end portion. The second axial end portion has a collapsed position and an expanded position. The second axial end portion extends axially into the first axial end portion and has a concave shape when in the collapsed position. The second axial end portion is convex when in the expanded position.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 6 is a schematic pictorial view of a collection device constructed in accordance with a second embodiment of the present invention;

FIG. 7 is a schematic pictorial view of a collection device constructed in accordance with a third embodiment of the present invention;

FIG. 8 is a schematic pictorial view of a collection device constructed in accordance with a fourth embodiment of the present invention;

FIG. 12 is a schematic sectional view of a collection device constructed in accordance with a seventh embodiment of the present invention;

FIG. 13 is a schematic sectional view of a collection device constructed in accordance with an eighth embodiment of the present invention;

FIG. 14 is a schematic sectional view of the collection device of FIG. 13 shown in a collapsed position; and FIG. 15 is a schematic pictorial view of a collection device constructed in accordance with a ninth embodiment of the present invention.

DETAILED OF THE INVENTION

Figure 3:
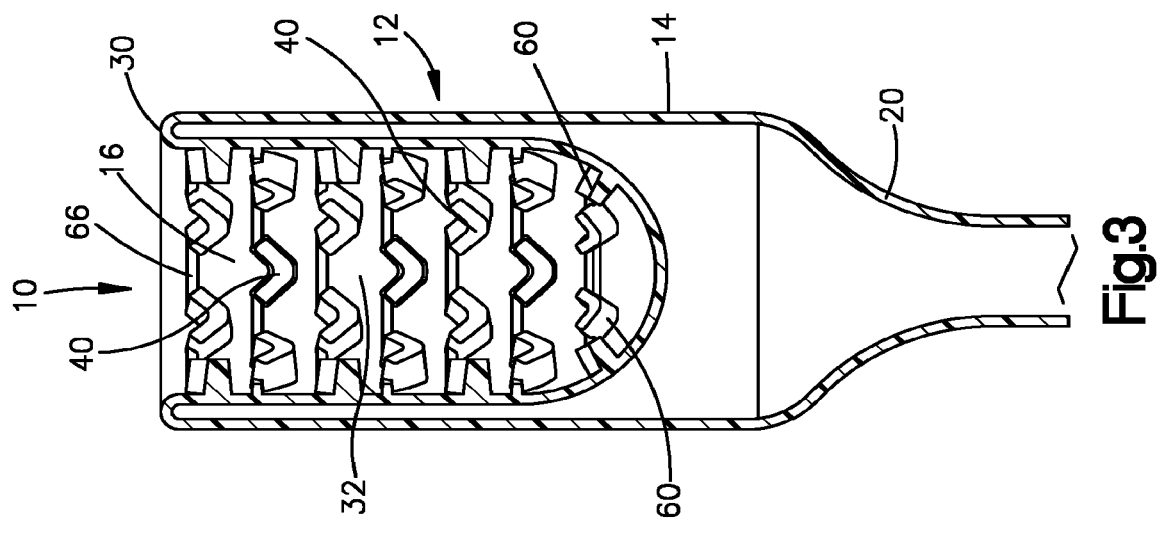
FIG. 3 is a sectional view of the collection device of FIG. 2.

A collection device 10 for the collecting a biological sample constructed in accordance with the present invention is illustrated in FIGS. 1-5. The collection device 10 may used to collect tissue, cells, protein, RNA and/or DNA from a body lumen, such as an esophagus of a patient. The tissue, cells, protein, RNA and/or DNA collected from the esophagus may be used in any one of the methods disclosed in U.S. patent application Ser. Nos. 14/109,041, 13/670,155, 13/263,020, U.S. Pat. Nos. 8,642,271, 8,481,707, 8,415,100, 8,221,977, 7,964,353, and 7,485,420, which are incorporated herein by reference in their entirety.

The collection device 10 includes a generally hollow longitudinally extending collection portion 12. The collection portion 12 has a first or proximal axial end portion 14 and a second or distal axial end portion 16. The proximal axial end portion 14 and the distal axial end portion 16 may be made of a flexible polymer, such as silicone or polyurethane. The distal axial end portion 16 has a lower durometer than the proximal axial end portion 14. The distal axial end portion 16 may expand and contract. The first or proximal axial end portion 14 is relatively rigid. Therefore, the proximal end portion 14 has a fixed radial extent. The first axial end portion 14 and the second axial end portion 16 may be integrally formed as one-piece or may be formed as separate pieces that are connected together in any desire manner. Although the proximal end portion 14 is illustrated as having a cylindrical shape, the proximal end portion may have any desired shape.

The proximal axial end portion 14 is connected to a support member 20, such as a catheter. The support member 20 may be a tubular member in fluid communication with the interior of the collection portion 12. The proximal axial end portion 14 conducts fluid, such as air, from the support member 20 to the distal axial end portion 16. A proximal end of the support 20 may be connected to a stopcock and syringe to control the injection of fluid to move the distal end portion 16 between the collapsed and expanded positions. The support 20 resists collapsing when a vacuum is applied to the support member and resists stretching during withdrawal of the collection device 10 from the collection site.

Figure 2:
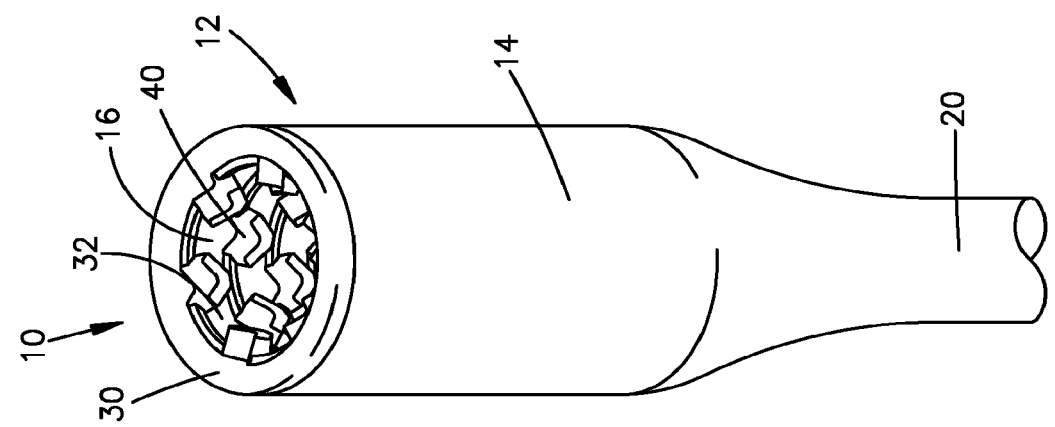
FIG. 2 is a schematic pictorial view of the collection device of FIG. 1 shown in a collapsed position.

The second or distal end portion 16 of the collection portion 12 has an expanded or inflated position (FIG. 1) and a collapsed or deflated position (FIGS. 2-3). The expanded position shown in FIG. 1 may be one of many expanded positions for the distal end portion 16. It is contemplated that the distal end portion 16 may expand more than shown in FIG. 1 so that the distal end portion obtains a more spherical shape and looks similar to a hot air balloon, see FIG. 15 for example. The distal end portion 16 has a convex shape, shown in FIG. 1, when in the expanded or inflated position. The distal end portion 16 may extend radially outward a greater distance than the proximal end portion 14 when in the expanded position.

The distal end portion 16 extends into the first or proximal axial end portion 14 and has a concave shape, shown in FIGS. 2 and 3, when in the collapsed or deflated position. The distal end portion 16 may be inverted when in the collapsed position. The distal end portion 16 extends axially into the interior of the proximal end portion 14 when in the collapsed or deflated position. Therefore, the distal end portion 16 moves axially or longitudinally relative to the proximal end portion 14 when moving between the deflated and inflated positions. The distal end portion 16 may be biased into the collapsed or deflated position in any desired manner.

The proximal end portion 14 has a relatively high durometer so that the proximal end portion does not collapse when a vacuum is applied to the proximal end portion through the support 20. The shape of the proximal end portion 14 does not change when the distal end portion 16 moves between the deflated and inflated positions. The proximal end portion 14 does not move radially when the distal end portion 16 moves between the deflated and inflated positions.

The distal end portion 16 of the collection portion 12 may be connected to the proximal end portion 14 by a circumferentially extending hinge 30. The hinge 30 may be a fold. The hinge 30 may extend circumferentially around the collection portion 12. The hinge 30 defines a distal axial end surface of the collection portion 12 when the distal end portion 16 is in the deflated or collapsed position. The distal end portion 16 defines an axial end surface of the collection portion 12 when the distal end portion is in the inflated or expanded position.

The distal end portion 16 has an outer surface 32 for collecting tissue when the distal portion is in the expanded position. The outer surface 32 faces radially outwardly when the distal end portion 16 is in the expanded position and may face radially inwardly when the distal end portion is in the collapsed or inverted position. It is contemplated that the outer surface 32 of the distal end portion 16 may have any desired construction for collecting tissue. The outer surface 32 of the distal end portion 16 may have a plurality of projections or bristles 40 for collecting tissue. The distal end portion 16 may have any desired number of projections or bristles 40.

Figure 1:
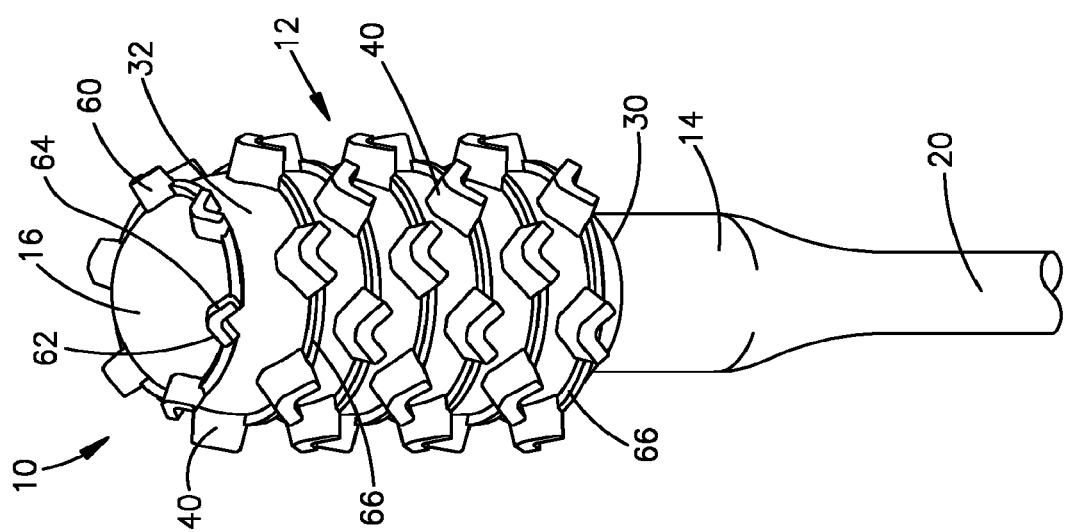
FIG. 1 is a schematic pictorial view of a biological sample collection device constructed in accordance with the present invention.
Figure 4:
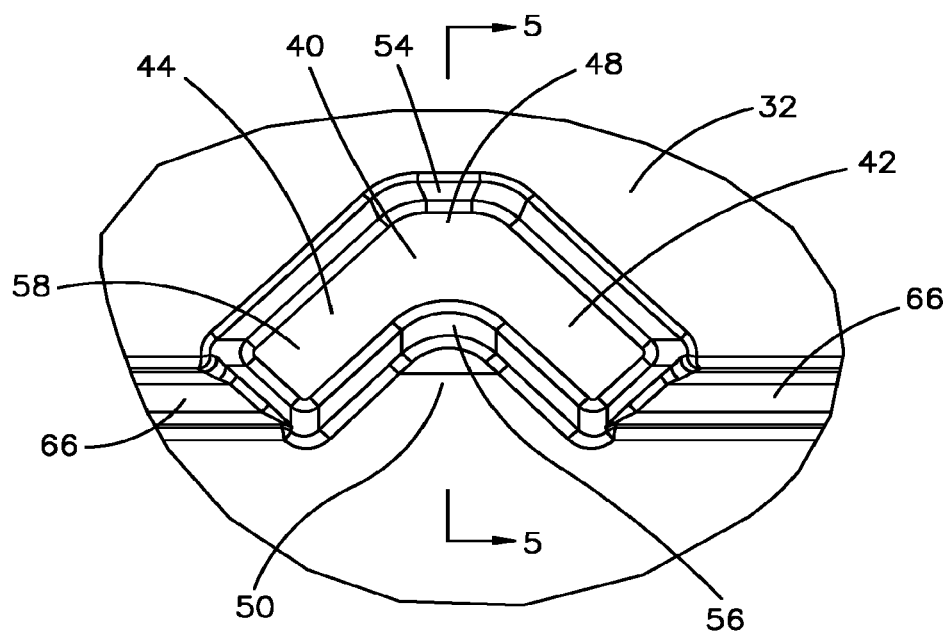
FIG. 4 is an enlarged plan view of a projection or bristle of the collection device
Figure 5:
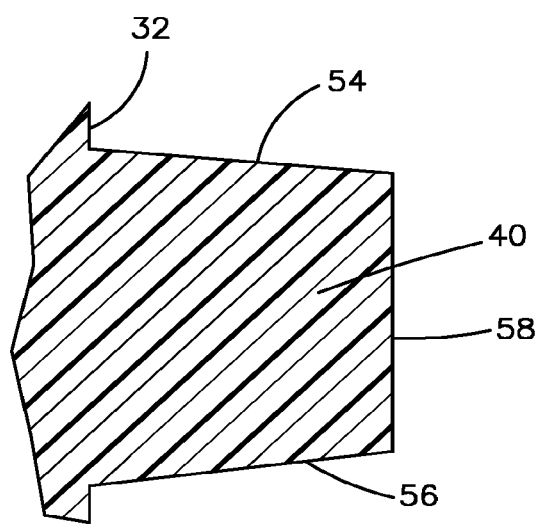
FIG. 5 is a sectional view of the projection taken along the line 5-5 in FIG. 4.

The projections or bristles 40 may have a V-shape (FIG. 4). Each projection 40 has a first side 42 and a second side 44 extending from an intersection 48. The first and second sides 42, 44 extend in a generally proximal direction from the intersection 48 when the distal end portion 16 is in the expanded position (FIG. 1). The first and second sides 42, 44 extend in a generally distal direction when the distal end portion 16 is in the collapsed or inverted position (FIGS. 2 and 3). The first and second sides 42, 44 define a cup 50 for receiving collected biological samples. The cup 50 faces in a proximal direction when the distal portion 16 is in the expanded position and faces in a distal direction when the distal portion is in the collapsed position.

The first and second sides 42, 44 may extend at an angle of approximately 90° relative to each other. It is contemplated that the first and second sides 42 and 44 may extend at any desired angle relative to each other. The desired angle may be determined based on the type of biological sample to be collected. Alternatively, the projections 40 may be cup shaped or have a semi-circular shape.

Each of the projections or bristles 40 has side walls 54 and 56 (FIG. 5) that extend radially outward from the outer surface 32 when the distal portion 16 is in the expanded position. The side walls 54 and 56 extend from the outer surface 32 to a radially outer surface 58 of the projection 40. The side walls 54 and 56 taper toward each other as the side walls extend from the outer surface 32 toward the radially outer surface 58 of the projection 40. It is contemplated that the side walls 54 and 56 may not taper toward each other.

The distal end portion 16 may include a plurality of projections or bristles 60 (FIG. 1) extending from a distal portion of the distal end portion 16. The projections 60 have the same general V-shape as the projections 40 and are smaller than the projections 40. The projections 60 have first and second sides 62 and 64 that have a length smaller than the first and second sides 42, 44 of the projections 40.

The projections or bristles 40, 60 are arranged in circumferentially extending rows (FIG. 1). It is contemplated that each row has six projections 40 or 60. It is contemplated that each of the rows may have any desired number of projections 40 or 60. Each of the projections 40, 60 is circumferentially offset from the projections on an adjacent row. Ribs 66 extend circumferentially between adjacent projections 40, 60 in each row. The ribs 66 extend between ends of the sides walls 54, 56 opposite the intersections 48.

The collection portion 12 is moved to a collection site within a body lumen, such as an esophagus, with the distal end portion 16 in the collapsed or deflated position. The collection portion 12 may be swallowed by a patient. It is also contemplated that the patient may be intubated with the collection portion 12 attached to a catheter. The distal end portion 16 may be held in the collapsed or deflated position by the hinge 30 and/or by applying a vacuum to the collection portion 12 through the support 20. The distal end portion 16 may also be held in the collapsed position by a cap or cover that falls off, pops off and/or dissolves when the collection portion 12 reaches the body lumen. The support member 20 or catheter may have depth markings to determine the collection site within the patient's anatomy. The distal end portion 16 is moved from the collapsed position to the expanded position when the collection portion 12 is at the collection site. A pressurized fluid, such as air, may be applied to the distal end portion 16 to cause the distal end portion to move axially from the collapsed position to the expanded position.

The collection portion 12 is moved in the body lumen to collect a biological sample, such as, tissue, cells, protein, RNA and/or DNA from the collection site when the distal portion is in the expanded position. It is contemplated that the collection portion 12 is only moved in a proximal direction so that the expanded distal end portion 16 engages the collection site to collect biological samples. The depth markings on the support member 20 or catheter may be used as a guide. After the biological sample is collected, the distal end portion 16 is moved from the expanded position to the collapsed or inverted position. The distal end portion 16 may be moved from the expanded position to the collapsed position by applying a vacuum to the collection portion 12. As the collection portion 12 moves out of the body lumen, the distal end portion 16 does not engage the body lumen and prevents the collected biological samples from being contaminated by tissue from areas along the body lumen different from the collection site. Once the collection device 10 is removed from the patient, the biological samples are collected via a wash and/or the collection portion 12 or the distal end portion 16 may be cut from the support member 20 and deposited in a biological sample vial.

A second exemplary embodiment of a collection device constructed in accordance with the present invention is illustrated in FIG. 6. The collection device of FIG. 6 is generally similar to the collection device of FIGS. 1-5. Accordingly, similar numerals will be used to describe similar components.

A collection device 110 (FIG. 6) includes a generally hollow longitudinally extending collection portion 112. The collection portion 112 has a first or proximal axial end portion 114 and a second or distal axial end portion 116. The distal axial end portion 116 may expand and contract. The proximal end portion 114 is relatively rigid. Therefore, the proximal end portion 114 has a fixed radial extent. The first axial end portion 114 and the second axial end portion 116 may be integrally formed as one-piece or may be formed as separate pieces that are connected together in any desired manner.

The proximal axial end portion 114 is connected to a support member 120, such as a catheter. The support member 120 may be a tubular member in fluid communication with the interior of the collection portion 112. The proximal end portion 114 conducts fluid, such as air, from the support member 120 to the distal axial end portion 116.

The second or distal end portion 116 of the collection portion 112 has an expanded or inflated position (FIG. 6) and a collapsed or deflated position similar to the position shown in FIGS. 2 and 3. The distal end portion 116 has a convex shape, shown in FIG. 6, when in the expanded or inflated position. The expanded position shown in FIG. 6 may be one of many expanded positions for the distal end portion 116. It is contemplated that the distal end portion 116 may expand more than shown in FIG. 6 so that the distal end portion obtains a more spherical shape and looks similar to a hot air balloon, see FIG. 15 for example.

The distal end portion 116 extends into the first or proximal end portion 114 and has a concave shape when in the collapsed or deflated position. The distal end portion 116 may be biased into the collapsed or deflated position in any desired manner. Therefore, the distal end portion 116 moves axially relative to the proximal end portion 114 when moving between the deflated and inflated positions. The shape of the proximal end portion 114 does not change when the distal end portion 116 moves between the deflated and inflated positions. The proximal end portion 114 does not move radially when the distal end portion 116 moves between the deflated and inflated positions.

The distal end portion 116 of the collection portion 112 may be connected to the proximal end portion 114 by a circumferentially extending hinge 130. The hinge 130 may be a fold. The hinge 130 may extend circumferentially around the collection portion 112. The hinge 130 defines a distal axial end surface of the collection portion 112 when the distal end portion 116 is in the deflated or collapsed position. The distal end portion 116 defines an axial end surface of the collection portion 112 when the distal end portion is in the inflated or expanded position.

The distal end portion 116 has an outer surface 132 for collecting biological samples. The outer surface 132 of the distal end portion 116 may have a plurality of projections or ribs 140 for collecting biological samples. The ribs 140 extend circumferentially around the distal end portion 116 and may extend generally parallel to each other. Although the outer surface 132 is shown as having seven projections or ribs 140, it is contemplated that the outer surface may have any desired number of ribs. The ribs 140 may extend radially from the outer surface 132 any distance. It is also contemplated that the ribs 140 may extend different distances from the outer surface 132.

A third exemplary embodiment of a collection device constructed in accordance with the present invention is illustrated in FIG. 7. The collection device of FIG. 7 is generally similar to the collection devices of FIGS. 1-6. Accordingly, similar numerals will be used to describe similar components.

A collection device 210 (FIG. 7) includes a generally hollow longitudinally extending collection portion 212. The collection portion 212 has a first or proximal axial end portion 214 and a second or distal axial end portion 216. The distal axial end portion 216 may expand and contract. The proximal end portion 214 is relatively rigid. Therefore, the proximal end portion 214 has a fixed radial extent. The first axial end portion 214 and the second axial end portion 216 may be integrally formed as one-piece or may be formed as separate pieces that are connected together in any desired manner.

The proximal end portion 214 has a fixed radial extent. The proximal axial end portion 214 is connected to a support member 220, such as a catheter. The support member 220 may be a tubular member in fluid communication with the interior of the collection portion 212. The proximal axial end portion 214 conducts fluid, such as air, from the support member 20 to the distal axial end portion 216.

The distal end portion 216 of the collection portion 212 has an expanded or inflated position (FIG. 7) and a collapsed or deflated position similar to the position shown in FIGS. 2 and 3. The expanded position shown in FIG. 7 may be one of many expanded positions for the distal end portion 216. It is contemplated that the distal end portion 216 may expand more than shown in FIG. 7 so that the distal end portion obtains a more spherical shape and looks similar to a hot air balloon, see FIG. 15 for example. The distal end portion 216 has a convex shape, shown in FIG. 7, when in the expanded or inflated position.

The distal end portion 216 extends into the proximal end portion 214 and has a concave shape when in the collapsed or deflated position. Therefore, the distal end portion 216 moves axially relative to the proximal end portion 214 when moving between the deflated and inflated positions. The distal end portion 216 may be biased into the collapsed or deflated position in any desired manner. The shape of the proximal end portion 214 does not change when the distal end portion 216 moves between the deflated and inflated positions. The proximal end portion 214 does not move radially when the distal end portion 216 moves between the deflated and inflated positions.

The distal end portion 216 of the collection portion 212 may be connected to the proximal end portion 214 by a circumferentially extending hinge 230. The hinge 230 may be a fold. The hinge 230 may extend circumferentially around the collection portion 212. The hinge 230 defines a distal axial end surface of the collection portion 212 when the distal end portion 216 is in the deflated or collapsed position. The distal end portion 216 defines an axial end surface of the collection portion 212 when the distal end portion is in the inflated or expanded position.

The distal end portion 216 has an outer surface 232 for collecting biological samples. The outer surface 232 of the distal end portion 216 may have a plurality of projections or bristles 240 for collecting biological samples. The projections 240 have a generally cylindrical shape. The outer surface 232 may have any desired number of projections 240. The projections 240 may extend radially from the outer surface 232 any distance. It is also contemplated that the projections 240 may extend different distances from the outer surface 232. The projections 240 may have any desired diameters and may have different diameters.

Figure 9:
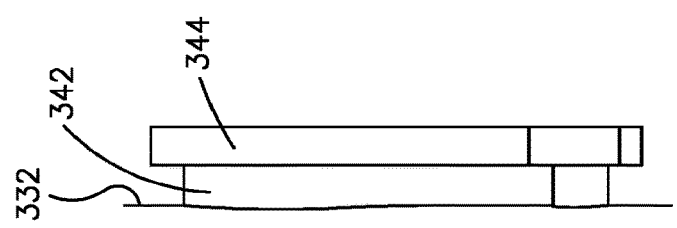
FIG. 9 is a side view of a projection of the collection device of FIG. 8.

A fourth exemplary embodiment of a collection device constructed in accordance with the present invention is illustrated in FIGS. 8 and 9. The collection device of FIGS. 8 and 9 is generally similar to the collection devices of FIGS. 1-7. Accordingly, similar numerals will be used to describe similar components.

A collection device 310 (FIGS. 8-9) includes a generally hollow longitudinally extending tissue collection portion 312. The collection portion 312 has a first or proximal axial end portion 314 and a second or distal axial end portion 316. The distal axial end portion 316 may expand and contract. The proximal end portion 314 is relatively rigid. Therefore, the proximal end portion 314 has a fixed radial extent. The first axial end portion 314 and the second axial end portion 316 may be integrally formed as one-piece or may be formed as separate pieces that are connected together in any desired manner.

The proximal end portion 314 has a fixed radial extent. The proximal axial end portion 314 is connected to a support member 320, such as a catheter. The support member 320 may be a tubular member in fluid communication with the interior of the collection portion 312. The proximal axial end portion 314 conducts fluid from the support member 320 to the distal axial end portion 316.

The distal end portion 316 of the collection portion 312 has an expanded or inflated position (FIG. 8) and a collapsed or deflated position similar to the position shown in FIGS. 2 and 3. The expanded position shown in FIG. 8 may be one of many expanded positions for the distal end portion 316. It is contemplated that the distal end portion 316 may expand more than shown in FIG. 8 so that the distal end portion obtains a more spherical shape and looks similar to a hot air balloon, see FIG. 15 for example. The distal end portion 316 has a convex shape, shown in FIG. 8, when in the expanded or inflated position.

The distal end portion 316 extends into the proximal end portion 314 and has a concave shape when in the collapsed or deflated position. Therefore, the distal end portion 316 moves axially relative to the proximal end portion 314 when moving between the deflated and inflated positions. The distal end portion 316 may be biased into the collapsed or deflated position in any desired manner. The shape of the proximal end portion 314 does not change when the distal end portion 316 moves between the deflated and inflated positions. The proximal end portion 314 does not move radially when the distal end portion 316 moves between the deflated and inflated positions.

The distal end portion 316 of the collection portion 312 may be connected to the proximal end portion 314 by a circumferentially extending hinge 330. The hinge 330 may be a fold. The hinge 330 may extend circumferentially around the collection portion 312. The hinge 330 defines a distal axial end surface of the collection portion 312 when the distal end portion 316 is in the deflated or collapsed position. The distal end portion 316 defines an axial end surface of the collection portion 312 when the distal end portion is in the inflated or expanded position.

The distal end portion 316 has an outer surface 332 for collecting biological samples. The outer surface 332 is generally cylindrical. The outer surface 332 has an axially extending surface 334 and an axial end surface 336. The axially extending surface 334 of the outer surface 332 may have a plurality of projections or bristles 340 for collecting tissue. It is contemplated that the axial end surface 336 may also include projections 340.

Each of the projections 340 has a support portion 342 (FIG. 9). The support portion 342 may have a bi-directional curve shape or S-shape extending radially outward from the outer surface 332. A bi-directional curve shaped or S-shaped portion 344 having a cross-section larger than the support portion 342 extends from the support portion, as shown in FIG. 9. The outer surface 332 may have any desired number of projections 340. The projections 340 may extend radially from the outer surface 332 any distance. It is also contemplated that the projections 340 may extend different distances from the outer surface 332.

Figure 10:
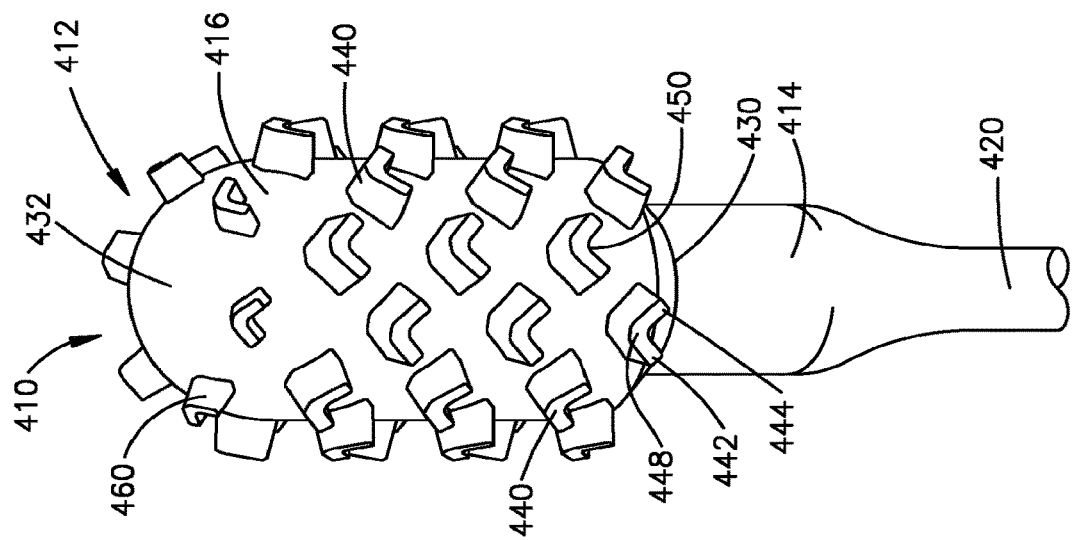
FIG. 10 is a schematic pictorial view of a collection device constructed in accordance with a fifth embodiment of the present invention.

A fifth exemplary embodiment of a collection device constructed in accordance with the present invention is illustrated in FIG. 10. The collection device of FIG. 10 is generally similar to the collection devices of FIGS. 1-9. Accordingly, similar numerals will be used to describe similar components.

A collection device 410 (FIG. 10) includes a generally hollow longitudinally extending collection portion 412. The collection portion 412 has a first or proximal axial end portion 414 and a second or distal axial end portion 416. The distal axial end portion 416 may expand and contract. The proximal end portion 414 is relatively rigid. Therefore, the proximal end portion 414 has a fixed radial extent. The first axial end portion 414 and the second axial end portion 416 may be integrally formed as one-piece or may be formed as separate pieces that are connected together in any desired manner.

The proximal end portion 414 has a fixed radial extent. The proximal axial end portion 414 is connected to a support member 420, such as a catheter. The support member 420 may be a tubular member in fluid communication with the interior of the collection portion 412. The proximal end portion 414 conducts fluid, such as air, from the support member 420 to the distal axial end portion 416.

The distal end portion 416 of the collection portion 412 has an expanded or inflated position (FIG. 10) and a collapsed or deflated position similar to the position shown in FIGS. 2 and 3. The expanded position shown in FIG. 10 may be one of many expanded positions for the distal end portion 416. It is contemplated that the distal end portion 416 may expand more than shown in FIG. 10 so that the distal end portion obtains a more spherical shape and looks similar to a hot air balloon, see FIG. 15 for example. The distal end portion 16 has a convex shape, shown in FIG. 10, when in the expanded or inflated position.

The distal end portion 416 extends into the proximal end portion and has a concave shape when in the collapsed or deflated position. Therefore, the distal end portion 416 moves axially relative to the proximal end portion 414 when moving between the deflated and inflated positions. The distal end portion 416 may be biased into the collapsed or deflated position in any desired manner. The shape of the proximal end portion 414 does not change when the distal end portion 416 moves between the deflated and inflated positions. The proximal end portion 414 does not move radially when the distal end portion 416 moves between the deflated and inflated positions.

The distal end portion 416 of the collection portion 412 may be connected to the proximal end portion 414 by a circumferentially extending hinge 430. The hinge 430 may be a fold. The hinge 430 may extend circumferentially around the collection portion 412. The hinge 430 defines a distal axial end surface of the collection portion 412 when the distal end portion 416 is in the deflated or collapsed position. The distal end portion 416 defines an axial end surface of the collection portion 412 when the distal end portion is in the inflated or expanded position.

The distal end portion 416 has an outer surface 432 for collecting biological samples. The outer surface 432 of the distal end portion 416 may have a plurality of projections or bristles 440 for collecting biological samples. The projections or bristles 440 may have a V-shape and be generally similar to the V-shaped projections 40 described in connection with the embodiment illustrated in FIGS. 1-5. Each projection 440 has a side 442 and a second side 444 extending in a generally proximal direction from an intersection 448 when the distal end portion 416 is in the expanded position. Therefore, the first and second sides 442, 444 define a proximally facing cup 450 for receiving collected tissue. The first and second sides 442, 444 extend at an angle to each other. The first and second sides 442, 444 may extend at an angle of approximately 90° relative to each other. It is contemplated that the first and second sides 442 and 444 may extend at any desired angle relative to each other. The desired angle may be determined based on the type of biological sample to be collected.

The distal end portion 416 may include a plurality of projections or bristles 460 extending from a distal portion of the distal end portion 416. The projections 460 have the same general V-shape as the projections 440. The projections 460 are smaller than the projections 440 and are located distally to the projections 440 when the distal end portion 416 is in the expanded position.

Figure 11:
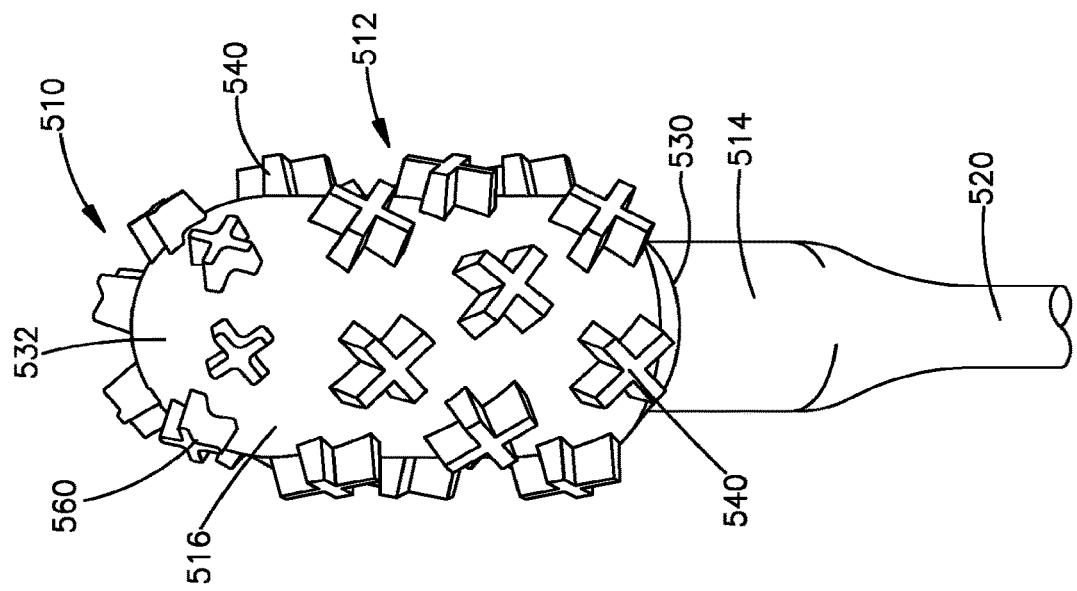
FIG. 11 is a schematic pictorial view of a collection device constructed in accordance with a sixth embodiment of the present invention.

A sixth exemplary embodiment of a collection device constructed in accordance with the present invention is illustrated in FIG. 11. The collection device of FIG. 10 is generally similar to the collection devices of FIGS. 1-10. Accordingly, similar numerals will be used to describe similar components.

A collection device 510 (FIG. 11) includes a generally hollow longitudinally extending collection portion 512. The collection portion 512 has a first or proximal axial end portion 514 and a second or distal axial end portion 516. The distal axial end portion 516 may expand and contract. The proximal end portion 514 is relatively rigid. Therefore, the proximal end portion 514 has a fixed radial extent. The first axial end portion 514 and the second axial end portion 516 may be integrally formed as one-piece or may be formed as separate pieces that are connected together in any desired manner.

The proximal end portion 514 has a fixed radial extent. The proximal axial end portion 514 is connected to a support member 520, such as a catheter. The support member 520 may be a tubular member in fluid communication with the interior of the collection portion 512. The proximal end portion 514 conducts fluid from the support member 520 to the distal axial end portion 516.

The distal end portion 516 of the collection portion 512 has an expanded or inflated position (FIG. 11) and a collapsed or deflated position similar to the position shown in FIGS. 2 and 3. The expanded position shown in FIG. 11 may be one of many expanded positions for the distal end portion 516. It is contemplated that the distal end portion 516 may expand more than shown in FIG. 11 so that the distal end portion obtains a more spherical shape and looks similar to a hot air balloon, see FIG. 15 for example. The distal end portion 16 has a convex shape, shown in FIG. 11, when in the expanded or inflated position.

The distal end portion 516 extends into the proximal end portion 514 and has a concave shape when in the collapsed or deflated position. Therefore, the distal end portion 516 moves axially relative to the proximal end portion 514 when moving between the deflated and inflated positions. The distal end portion 516 may be biased into the collapsed or deflated position in any desired manner. The shape of the proximal end portion 514 does not change when the distal end portion 516 moves between the deflated and inflated positions. The proximal end portion 514 does not move radially when the distal end portion 516 moves between the deflated and inflated positions.

The distal end portion 516 of the collection portion 512 may be connected to the proximal end portion 514 by a circumferentially extending hinge 530. The hinge 530 may be a fold. The hinge 530 may extend circumferentially around the collection portion 512. The hinge 530 defines a distal axial end surface of the collection portion 512 when the distal end portion 516 is in the deflated or collapsed position. The distal end portion 516 defines an axial end surface of the collection portion 512 when the distal end portion is in the inflated or expanded position.

The distal end portion 516 has an outer surface 532 for collecting biological samples. The outer surface 532 of the distal end portion 516 may have a plurality of projections or bristles 540 for collecting biological samples. The projections or bristles 540 may have an X-shape. The distal end portion 516 may include a plurality of projections or bristles 560 extending from a distal portion of the distal end portion 516. The projections 560 have the same general X-shape as the projections 540. However, the projections 560 are smaller than the projections 540.

A seventh exemplary embodiment of a collection device constructed in accordance with the present invention is illustrated in FIG. 12. The collection device of FIG. 12 is generally similar to the collection devices of FIGS. 1-11. Accordingly, similar numerals will be used to describe similar components.

A collection device 610 (FIG. 12) includes a generally hollow longitudinally extending collection portion 612. The collection portion 612 has a first or proximal axial end portion 614 and a second or distal axial end portion 616. The distal axial end portion 616 may expand and contract. The proximal end portion 614 is relatively rigid. Therefore, the proximal end portion 614 has a fixed radial extent.

The proximal axial end portion 614 is connected to a support member, such as a catheter. The support member may be a tubular member in fluid communication with the interior of the collection portion 612. The proximal end portion 614 conducts fluid from the support member to the distal end portion 616.

The distal end portion 616 has a first axial end portion 622 connected to the proximal axial end portion 614. The first end portion 622 may be connected to the proximal end portion 614 in any desired manner, such as by using an adhesive. The first axial end portion 622 engages a shoulder 624 on the proximal axial end portion 614. Therefore, the collection portion 612 has a smooth outer surface.

The distal end portion 616 of the collection portion 612 has an expanded or inflated position (FIG. 12) and a collapsed or deflated position similar to the position shown in FIGS. 2 and 3. The expanded position shown in FIG. 12 may be one of many expanded positions for the distal end portion 616. It is contemplated that the distal end portion 616 may expand more than shown in FIG. 12 so that the distal end portion obtains a more spherical shape and looks similar to a hot air balloon, see FIG. 15 for example. The distal end portion 16 has a convex shape, shown in FIG. 12, when in the expanded or inflated position.

The distal end portion 616 extends into the proximal end portion 614 and has a concave shape when in the collapsed or deflated position. Therefore, the distal end portion 616 moves axially relative to the proximal end portion 614 when moving between the deflated and inflated positions. The distal end portion 616 may be biased into the collapsed or deflated position in any desired manner. The shape of the proximal end portion 614 does not change when the distal end portion 616 moves between the deflated and inflated positions. The proximal end portion 614 does not move radially when the distal end portion 616 moves between the deflated and inflated positions.

The distal end portion 616 of the collection portion 612 may be connected to the proximal end portion 614 at a circumferentially extending hinge 630. The hinge 630 may extend circumferentially around the collection portion 612. The hinge 630 defines a distal axial end surface of the collection portion 612 when the distal end portion 616 is in the deflated or collapsed position. The distal end portion 616 defines an axial end surface of the collection portion 612 when the distal end portion is in the inflated or expanded position.

The distal end portion 616 has an outer surface 632 for collecting biological samples. It is contemplated that the outer surface 632 of the distal end portion 616 may have any desired construction for collecting biological samples. The outer surface 632 of the distal end portion 616 may have a plurality of projections or bristles for collecting biological samples. The projections or bristles may have any desired shape, such as the shapes shown in FIGS. 1-11.

An eighth exemplary embodiment of a collection device constructed in accordance with the present invention is illustrated in FIGS. 13-14. The collection device of FIGS. 13-14 is generally similar to the collection devices of FIGS. 1-12. Accordingly, similar numerals will be used to describe similar components.

A collection device 710 (FIG. 11) includes a generally hollow longitudinally extending collection portion 712. The collection portion 712 has a first or proximal axial end portion 714 and a second or distal axial end portion 716. The distal axial end portion 716 may expand and contract. The proximal end portion 714 is relatively rigid. Therefore, the proximal end portion 714 has a fixed radial extent. The first axial end portion 714 and the second axial end portion 716 may be integrally formed as one-piece or may be formed as separate pieces that are connected together in any desired manner.

The proximal end portion 714 has a fixed radial extent. The proximal axial end portion 714 is connected to a support member 720. The support member 720 may be a tubular member in fluid communication with the interior of the collection portion 712. The proximal end portion 714 conducts fluid from the support member 720 to the distal end portion 716.

The distal end portion 716 of the collection portion 712 has an expanded or inflated position (FIG. 13) and a collapsed or deflated position (FIG. 14). The expanded position shown in FIG. 13 may be one of many expanded positions for the distal end portion 716. It is contemplated that the distal end portion 716 may expand more than shown in FIG. 13 so that the distal end portion obtains a more spherical shape and looks similar to a hot air balloon, see FIG. 15 for example. The distal end portion 716 has a convex shape, shown in FIG. 13, when in the expanded or inflated position.

The distal end portion 716 extends into the proximal end portion 714 and has a concave shape when in the collapsed or deflated position, as shown in FIG. 14. The distal end portion 716 only moves axially relative to the proximal end portion 714 when moving between the deflated and inflated positions. The distal end portion 716 may be biased into the collapsed or deflated position in any desired manner. The shape of the proximal end portion 714 does not change when the distal end portion 716 moves between the deflated and inflated positions. The proximal end portion 714 does not move radially when the distal end portion 716 moves between the deflated and inflated positions.

The distal end portion 716 of the collection portion 712 may be connected to the proximal end portion 714 by a circumferentially extending hinge 730. The hinge 730 may be a fold. The hinge 730 may extend circumferentially around the collection portion 712. The hinge 730 defines a distal axial end surface of the collection portion 712 when the distal end portion 716 is in the deflated or collapsed position. The distal end portion 716 defines an axial end surface of the collection portion 712 when the distal end portion is in the inflated or expanded position.

The distal end portion 716 has an outer surface 732 for collecting biological samples. It is contemplated that the outer surface 732 of the distal end portion 716 may have any desired construction for collecting biological samples. The outer surface 732 of the distal end portion 716 may have a plurality of projections or bristles 740 for collecting biological samples. The outer surface 732 may have any desired number of projections 740.

A ninth exemplary embodiment of a collection device constructed in accordance with the present invention is illustrated in FIG. 15. The collection device of FIG. 15 is generally similar to the collection device of FIGS. 1-14. Accordingly, similar numerals will be used to describe similar components.

A collection device 810 (FIG. 15) includes a generally hollow longitudinally extending collection portion 812. The collection portion 812 has a first or proximal axial end portion 814 and a second or distal axial end portion 816. The distal axial end portion 816 may expand and contract. The proximal end portion 814 is relatively rigid. Therefore, the proximal end portion 814 has a fixed radial extent. The first axial end portion 814 and the second axial end portion 816 may be integrally formed as one-piece or may be formed as separate pieces that are connected together in any desired manner.

The proximal axial end portion 814 is connected to a support member 820, such as a catheter. The support member 820 may be a tubular member in fluid communication with the interior of the collection portion 812. The proximal end portion 814 conducts fluid, such as air, from the support member 820 to the distal axial end portion 816.

The second or distal end portion 816 of the collection portion 812 has an expanded or inflated position (FIG. 15) and a collapsed or deflated position similar to the position shown in FIGS. 2 and 3. The distal end portion 816 has a convex shape, shown in FIG. 15, when in the expanded or inflated position. The expanded position shown in FIG. 15 may be one of many expanded positions for the distal end portion 816. It is contemplated that the distal end portion 816 may expand less than shown in FIG. 15 so that the distal end portion obtains a more oblong shape and looks similar to the distal end portion 16 shown in FIG. 1.

The distal end portion 816 extends into the first or proximal end portion 814 and has a concave shape when in the collapsed or deflated position. The distal end portion 816 may be biased into the collapsed or deflated position in any desired manner. Therefore, the distal end portion 816 moves axially relative to the proximal end portion 814 when moving between the deflated and inflated positions. The shape of the proximal end portion 814 does not change when the distal end portion 816 moves between the deflated and inflated positions. The proximal end portion 814 does not move radially when the distal end portion 816 moves between the deflated and inflated positions.

The distal end portion 816 of the collection portion 812 may be connected to the proximal end portion 814 by a circumferentially extending hinge 830. The hinge 830 may be a fold. The hinge 830 may extend circumferentially around the collection portion 812. The hinge 830 defines a distal axial end surface of the collection portion 812 when the distal end portion 816 is in the deflated or collapsed position. The distal end portion 816 defines an axial end surface of the collection portion 812 when the distal end portion is in the inflated or expanded position. The distal end portion 816 has an outer surface 832 for collecting biological samples. The outer surface 832 of the distal end portion 816 may have a textured surface or include a plurality of projections or ribs for collecting biological samples.

Each of the collection portions of the described collection devices is moved to a collection site within a body lumen, such as an esophagus, with the distal end portion in the collapsed or deflated position. The collection portion may be swallowed by a patient. The distal end portion may be held in the collapsed or deflated position by the hinge and/or by applying a vacuum to the collection portion through the support. The distal end portion may also be held in the collapsed position by a cap or cover that falls off, pops off and/or dissolves when the collection portion reaches the collection site. The distal end portion is moved from the collapsed position to the expanded position when the collection portion is at the collection site. The collection portion is moved in the body lumen to collect biological samples, such as, tissue, cells, protein, RNA and/or DNA from the collection site when the distal portion is in the expanded position. After the biological sample is collected, the distal end portion is moved from the expanded position to the collapsed position. As the collection portion moves out of the body lumen, the distal end portion does not engage the body lumen and prevents the collected biological samples from being contaminated by tissue from areas along the body lumen different from the collection site.

The collection devices described above may be formed as one-piece or formed as separate pieces that are connected together. Also, it is contemplated that the projections or bristles may have any desired shape. Accordingly, the tissue collection devices may have at least one V-shaped projection and/or at least one circumferentially extending rib and/or at least one cylindrical projection and/or at least one bi-directional curved shaped projection and/or at least one X-shaped projection. It is also contemplated that each of the collection devices may have circumferentially extending ribs extending between adjacent projections.

From the above description of the invention, those skilled in the art will perceive improvements, changes and modifications. Such improvements, changes and modifications are intended to be covered by the appended claims.

What is claimed is:

1. A device for collecting a biological sample in a patient, the device comprising
    a support through which fluid can be directed from a source;
    a collection portion in fluid communication with the support and being integral therewith, the collection portion having a first rigid axial end portion, a second expandable axial end portion, and a circumference relatively larger than that of the support while being sized to be swallowed by the patient,
    a first set of projections positioned on the second axial end portion in spaced relation to one another and being arranged in rows, each of the projections respectively defining a proximally facing cup having sidewalls to collect, receive, and hold the biological sample when the device is moved axially in a proximal direction along a site of interest; and
    circumferentially extending ribs which extend between adjacent rows of the rows of the first set of projections.

2. A device for collecting a biological sample as set forth in claim 1, wherein the second axial end portion includes a collapsed position and an expanded position, the second axial end portion being capable of moving in an axial direction relative to the first axial end portion when the second axial end portion moves between the collapsed position and the expanded position, each of the projections being designed to collect, receive, and hold the biological sample when the device is in the expanded position and is moved axially in the proximal direction along the site of interest.

3. A device for collecting a biological sample as set forth in claim 2 wherein each of the first set of projections respectively define the proximally facing cup when in the expanded position and a distally facing cup when in the collapsed position.

4. A device for collecting a biological sample as set forth in claim 1 wherein the sidewalls of the proximally facing cup, of each projection of the first set of projections, converge to form a V-shape.

5. A device for collecting a biological sample as set forth in claim 1 wherein the sidewalls of the projections of the first set of projections taper toward each other as the sidewalls extend radially outward from the collection portion.

6. A method for collecting a biological sample from a collection site of a lumen of a patient, the method comprising:
    providing a support through which fluid can be directed from a source and a collection portion in fluid communication with the support and being integral therewith, the collection portion having a circumference relatively larger than that of the support, a first rigid axial end portion, and a second expandable axial end portion having a collapsed position extending axially into the first axial end portion, the second axial end portion including a first set of tissue collecting projections, in spaced relation to one another and being arranged in rows, and circumferentially extending ribs which extend between adjacent rows of the rows of the first set of projections;

moving the support and the collection portion into the lumen of the patient, by swallowing of the collection portion, the second axial end portion is advanced into the lumen of the patient in the collapsed position;

axially moving the second axial end portion relative to the first axial end portion from the collapsed position into an expanded position to expose the first set of tissue collecting projections, each of the projections respectively defining a proximally facing cup having sidewalls to collect, receive, and hold the biological sample while in the expanded position;

collecting the biological sample with the first set of tissue collecting projections of the second axial end portion when the second axial end portion is in the expanded position;

collapsing the second axial end portion into the first axial end portion; and withdrawing the collection portion from the lumen of the patient.

7. A method for collecting a biological sample from a lumen as set forth in claim 6 wherein the first set of tissue collecting projections engage a surface of the collection site of the lumen of the patient to collect the biological sample.

8. A method for collecting a biological sample from a lumen as set forth in claim 7 wherein the step of collapsing the second axial end portion into the first axial end portion includes cupping the collected biological sample with the first set of tissue collecting projections.

9. A method for collecting a biological sample from a lumen as set forth in claim 6 wherein the step of collecting the biological sample includes collecting cells.

10. A method for collecting a biological sample from a lumen as set forth in claim 6 wherein the step of collecting the biological sample includes collecting DNA and/or RNA.

11. A method for collecting a biological sample from a lumen as set forth in claim 6 wherein the step of axially moving the second axial end portion from the collapsed position into the expanded position includes moving the second axial end portion from a concave shape to a convex shape.

12. A method for collecting a biological sample from a lumen as set forth in claim 6 wherein the step of collapsing the second axial end portion includes moving the second axial end portion from a convex shape to a concave shape.

13. A method for collecting a biological sample from a lumen as set forth in claim 6 wherein the step of collapsing the second axial end portion includes causing the first set of tissue collecting projections of the second axial end portion facing radially outwardly when the second axial end portion is in the expanded position to face radially inwardly when the second axial end portion is in the collapsed position.

14. A method for collecting a biological sample from a lumen as set forth in claim 6, wherein the lumen is an esophagus of the patient.

15. A method for collecting a biological sample from a lumen as set forth in claim 6 wherein the step of withdrawing the collection portion from the lumen of the patient includes preventing the second axial end portion of the collection portion from engaging the lumen at an area different from the collection site.

16. A method for collecting a biological sample from a lumen as set forth in claim 6 wherein the step of collapsing the second axial end portion into the first axial end portion includes applying a vacuum to the second axial end portion and the step of axially moving the second axial end portion relative to the first axial end portion from the collapsed position into the expanded position includes applying pressurized air to the collection portion.

17. A method for collecting a biological sample from a lumen as set forth in claim 6 wherein each of the first set of tissue collecting projections respectively define a distally facing cup when in the collapsed position.

18. A sample collection device for collecting a sample in a patient, the device comprising a support through which fluid can be directed from a source;

a collection portion in fluid communication with the support and being integral therewith, the collection portion having a first rigid axial end portion, a second expandable axial end portion, and a circumference relatively larger than that of the support while being configured to be swallowed by the patient;

a first set of projections and a second set of projections each positioned on the second axial end portion, the first set of projections in spaced relation to one another and being arranged in rows, the first set of projections and the second set of projections having different shapes, each of the first set of projections respectively defining a proximally facing cup having sidewalls to collect, receive and hold the sample when the device is moved axially in a proximal direction within the patient; and circumferentially extending ribs which extend between adjacent rows of the rows of the first set of projections.

19. A sample collection device for collecting a sample as set forth in claim 18, wherein the second axial end portion includes a collapsed position and an expanded position, the second axial end portion being capable of moving in an axial direction relative to the first axial end portion when the second axial end portion moves between the collapsed position and the expanded position.

20. A sample collection device for collecting a sample as set forth in claim 19, wherein each of the second set of projections respectively define a proximally facing cup when in the expanded position and a distally facing cup when in the collapsed position.

21. A sample collection device for collecting a sample as set forth in claim 18, wherein the first set of projections in a row adjacent to the second set of projections are offset from one another on the second axial end portion.

22. A sample collection device for collecting a sample as set forth in claim 18, wherein the second set of projections is a plurality of sets of projections and each respective set of projections of the second set of projections is axially aligned at different axial locations on the second axial end portion.

* * * * *